United States Patent
Crossley

(10) Patent No.: US 6,551,346 B2
(45) Date of Patent: Apr. 22, 2003

(54) METHOD AND APPARATUS TO PREVENT INFECTIONS

(76) Inventor: Kent Crossley, 1245 Delaware Ave., St. Paul, MN (US) 55118

( * ) Notice: Subject to any disclaimer, the term of this patent is extended or adjusted under 35 U.S.C. 154(b) by 21 days.

(21) Appl. No.: 09/812,519

(22) Filed: Mar. 20, 2001

(65) Prior Publication Data

US 2001/0047195 A1 Nov. 29, 2001

Related U.S. Application Data

(63) Continuation-in-part of application No. 09/572,999, filed on May 17, 2000.

(51) Int. Cl.[7] ............................................... A61B 18/18
(52) U.S. Cl. ............................... 607/88; 607/89; 606/2; 606/3; 606/10; 606/15; 604/20; 422/22; 422/24; 422/186
(58) Field of Search ........................ 606/1, 2, 3–7, 606/9–17; 607/88, 89; 604/20, 22, 48; 422/22, 24, 28, 186, 186.3

(56) References Cited

U.S. PATENT DOCUMENTS

| 4,318,883 A | 3/1982 | Polony et al. |
| 4,456,452 A | 6/1984 | Holzle et al. |
| 5,061,255 A | 10/1991 | Greenfeld et al. |
| 5,132,101 A | 7/1992 | Vogel et al. |
| 5,240,675 A | 8/1993 | Wilk et al. |
| 5,260,020 A | * 11/1993 | Wilk et al. .................... 606/15 |
| 5,445,608 A | 8/1995 | Chen et al. |
| 5,478,339 A | 12/1995 | Tadir et al. |
| 5,637,877 A | 6/1997 | Sinofsky |
| 5,714,119 A | 2/1998 | Kawagoe et al. |
| 5,855,203 A | 1/1999 | Matter |
| 5,947,958 A | 9/1999 | Woodard et al. |
| 6,107,326 A | * 8/2000 | Jori ............................ 514/410 |

FOREIGN PATENT DOCUMENTS

| DE | 30 23 130 A1 | 1/1982 |
| WO | WO 95/07451 | 3/1996 |
| WO | WO 96/23543 | 8/1996 |
| WO | WO 98/06456 | 2/1998 |

* cited by examiner

Primary Examiner—David M Shay
(74) Attorney, Agent, or Firm—Cesari and McKenna, LLP

(57) ABSTRACT

A photosensitizer together with complementary light energy are used to prevent the development of infection associated with an indwelling medical catheter or device. Light of a selected wavelength or wavelength band is coupled to the catheter or device and transmitted by a wall or walls thereof to one or both of the external and internal surfaces thereof. The catheter or device also incorporates at least one photosensitizer which releases a toxic substance when activated by the light energy which destroys bacteria on or around the catheter or device. A method of preventing infection using photosensitizers and complementary light energy is also disclosed.

36 Claims, 3 Drawing Sheets

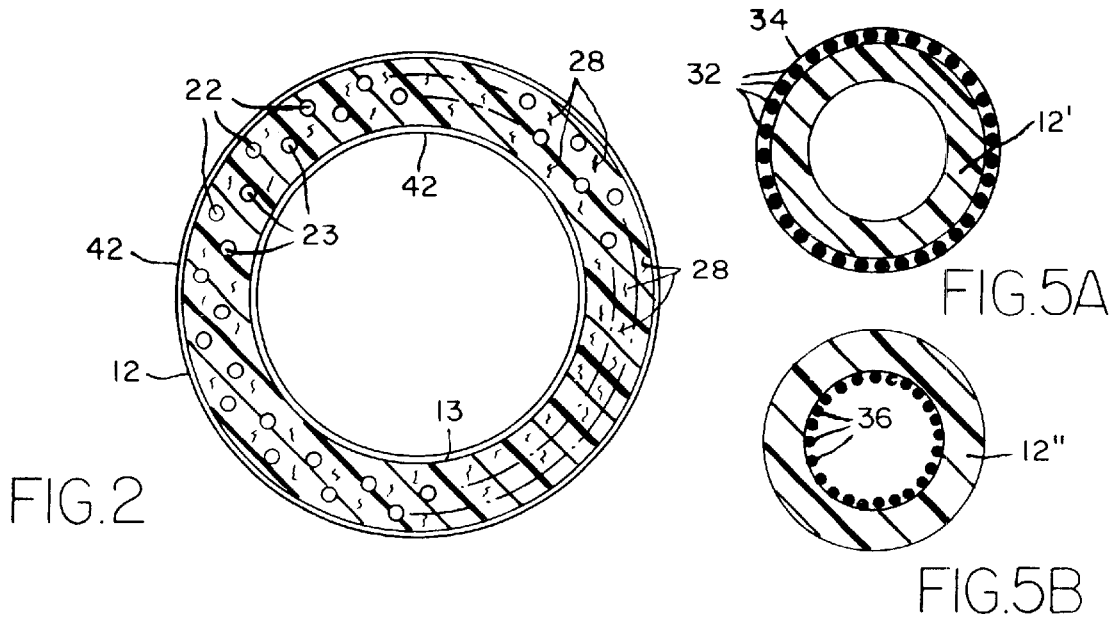
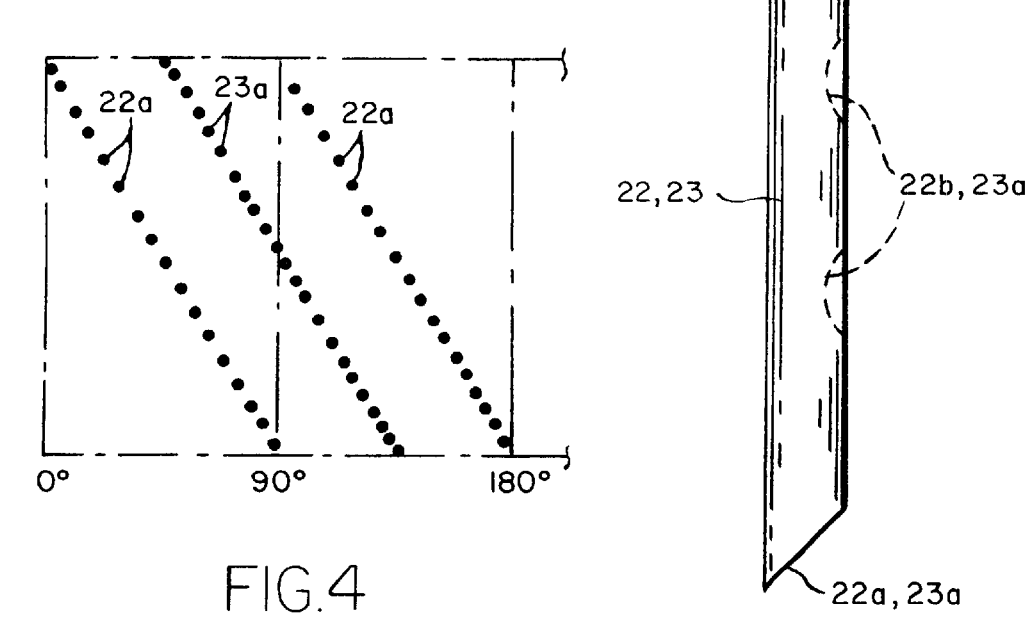

METHOD AND APPARATUS TO PREVENT INFECTIONS

RELATED APPLICATION

This application is a continuation-in-part of Ser. No. 09/572,999, filed May 17, 2000, now abandoned.

BACKGROUND OF THE INVENTION

The invention relates a method and apparatus for inhibiting or eliminating the development of colonization by microorganisms on tissue and indwelling medical devices and the subsequent occurrence of infections associated with same.

1. Field of the Invention

Infections associated with medical care are a major cause of morbidity and mortality. These infections are typically very costly to manage and may be associated with a variety of adverse outcomes including death. Common types of infections that develop in an acute care setting include pneumonia, urinary tract infection, wound infection and blood stream infection. Often these infections develop from the use of invasive devices in patients with limited resistance to infection as a result of their underlying illnesses or drug therapy.

Also, because many strains of microorganisms acquired in the hospital are resistant to commonly used antibiotics, it is often difficult and costly to treat these infections.

Medical catheter or device-related infections such as those associated with urinary, intravenous, intraarterial, dialysis and other types of medical catheters or other implanted medical devices usually result because of a breech of natural protective mechanisms present at sites such as the skin or the urethra. In these situations, the development of infection is believed to involve the following steps:

1. Microorganisms colonize and multiply on the patient's skin. There is a microbial flora normally present on the skin. However, when a patient is admitted to a health care setting, organisms from this environment (typically resistant to antimicrobials) become part of the patient's flora soon after admission;
2. After insertion of a catheter or other medical device, these organisms continue to multiply and begin to colonize the surface of the catheter or device;
3. As the organisms continue to multiply, they spread on the external and/or internal surface of the catheter or device and eventually into normally sterile tissues (e.g. blood vessels, abdomen, bladder, etc.). This process is facilitated by development of a biofilm (which consists of proteins from the blood or tissue fluid and other debris) on the surfaces of the devices;
4. Once in these normally sterile sites, the organisms continue to multiply and development of a clinical infection may result.

It has been known for many years that *Staphylococcus aureus*, for example, nearly always can be found to colonize the patients that develop infection with this organism, colonization meaning the presence of organism without evidence of infection.

The most important site for colonization is the anterior part of the nose (anterior nares). Individuals that develop a staphylococcal infection at the site of a wound, an indwelling catheter or prosthetic device usually has nasal colonization with this organism.

2. Description of the Prior Art

A variety of techniques have been used in an attempt to reduce the frequency of those infections. These have included impregnating catheters and devices with antibiotics, incorporating silver or silver compounds in the catheters and making the catheters or devices of different materials, e.g. silastic, and applying an electric current to the catheter. Each of these prior methods has, to some extent, reduced the frequency of infection. However none of these prior techniques is ideal. An ongoing concern is that microorganisms have the potential to develop resistance to the antimicrobials incorporated into the catheter or device in an attempt to prevent infection.

It is also known that various portions of the electromagnetic spectrum that include light are known to effectively kill microorganisms. Thus, white light radiation has been used in the treatment of nose and throat passages and ultraviolet light has been used to kill airborne bacteria, especially on tuberculosis wards. Although not extensively studied, light of other wavelengths is also capable of killing microorganisms.

Photodynamic therapy is the use of light with certain chemicals that are activated by the light energy. The chemicals that are used (referred to as photosensitizers) may be naturally occurring compounds (e.g. porphyrins, polyynes, psoralens and anthraquinones), dyes (e.g. methylene blue, Bengal Rose, toluidine blue, rhodamines, etc.) or other unrelated agents (e.g. cyanine compounds), that have antimicrobial activity alone or on exposure to light.

Light energy, which for purposes of this application means that part of the spectrum between 200 nm and 1400 nm which includes ultraviolet, visible and infrared light, acts on these chemical substances in different ways to result in an antimicrobial effect. Most often, the effect is to liberate an activated oxygen molecule (so-called singlet oxygen) which is able to destroy both cells and tissues. For each photosensitizer, there is a corresponding wavelength of light that causes optimal activation. For example, toluidine blue is optimally activated at a wavelength of about 626 nm. The wavelength at which there is a maximum effect may be modified by manipulating the photosensitizer molecule; alkyl substitution of the amino groups and halogenation of the chromagen both increase the wavelength associated with maximum activity.

The light energy may be laser generated or from another source such as an incandescent, fluorescent or halogen bulb or a light emitting diode. It may be of narrow spectrum or may include differing wavelengths and it may be pulsed or constant. With light in the ultraviolet part of the spectrum, it is known that pulsed light allows bacterial killing at energy levels orders of magnitude less than required with constant light.

Photosensitizers have differing degrees of activity against both bacteria and tissues. Some are more selectively active against microorganisms and are less toxic to tissues. Other photosensitizers are quite toxic to tissues. Photosensitizers that are tissue toxic have been used with light administration in the treatment of a variety of tumors. Although most of the recognized photosensitizers are antimicrobial, the mechanism of action varies somewhat. For example, methylene blue causes fatal changes in the nucleic acid in Proteus.

Chemical modification of the photosensitizers (e.g. differing side chains, molecular size, etc.) significantly impacts their activity. For example, among the furanocoumarin photosensitizers, replacement of an oxygen with sulfur or selenium is associated with markedly increased photoactivity. Dimethyl-methylene blue is substantially more active than methylene blue against most bacteria. Also, the lethal effect may be modified by the presence of various inorganic salts.

In addition to the activity of light on bacteria and other microorganisms (alone or with a photosensitizer), light energy may also have other effects that are beneficial in preventing or limiting infection. For example, ultraviolet light is able to markedly reduce the adhesion of bacteria to surfaces and to limit the development of biofilms. In addition, exposure to light may limit production of toxic bacterial substances, such as super antigens produced by Gram-positive bacteria.

Despite the fact that photodynamic therapy has been known for many years, we know of no implementations of that therapy that are effective to inhibit colonization of tissues with microorganisms and prevent infections associated with implanted medical catheters and devices.

SUMMARY OF THE INVENTION

Accordingly, it is an object of the invention to inhibit or eliminate the colonization of tissues with harmful microorganism.

Another object of the present invention to provide an improved method to prevent infection associated with in-dwelling medical catheters and devices.

Still another object of the invention is to provide an improved medical catheter or device which prevents infections commonly associated with the implantation of same.

A further object of the invention is to provide such a medical catheter or device which has an inherent antimicrobial activity that prevents the colonization by bacteria on the surfaces of the in-dwelling catheter or device and tissue adjacent thereto.

Yet another object of the invention is to provide a medical catheter or device of this type whose antimicrobial activity may be tailored to the particular microorganisms likely to be present at its dwelling site.

Other objects will, in part, be obvious and will, in part, appear hereinafter.

The invention accordingly comprises the several steps and the relation of one or more of such steps with respect to each of the others, and the apparatus embodying the features of construction, combination of elements and arrangement of parts which are adapted to effect such steps, all as exemplified in the following detailed description, and the scope of the invention will be indicated in the claims.

Briefly in accordance with my invention, light energy together with a photosensitizer or photosensitizers is used to prevent the development of infection at the site of an in-dwelling medical catheter or device. More particularly, light of a selected wavelength or wavelength band is coupled to a catheter or device and transmitted by a wall or walls thereof or to either or both external and internal surfaces thereof. The wavelength of the light is selected so that when the catheter or device is indwelling in a patient, the light illuminating the surface(s) and tissue has a toxic effect on microorganisms that tend to build up on the surface(s) at the implantation site. The catheter or device itself also incorporates a photo sensitizer(s) which releases a toxic substance at the surface(s) which is activated by the light energy thereby increasing the antimicrobial activity of the catheter or device.

For purposes of this application, a "catheter" means any cannula with one or more lumens used to 1) deliver fluid and drugs to the vascular system or other tissues (e.g. the cerebrospinal fluid), 2) access the vascular system for various reasons (e.g. pressure monitoring, hemodialysis) or 3) irrigate or drain body tissue. Examples of such tissues include bladder, abdomen, chest cavity, intracranial or intrathecal cavities, wounds, joints, etc. The word "device" refers to types of medical equipment other than catheters that are normally inserted into sterile tissues, examples being nose and throat applications, stents, cardiac pacing leads and the like.

BRIEF DESCRIPTION OF THE DRAWINGS

For a fuller understanding of the nature and objects of the invention, reference should be made to the following detailed description taken in connection with the accompanying drawings, in which:

FIG. 2 is a sectional view on a larger scale taken along the line 2—2 of FIG. 1;

FIG. 3 is a fragmentary perspective view on a still larger scale showing an optical fiber in the FIG. 1 catheter in greater detail;

FIG. 4 is a diagrammatic view illustrating the distribution of optical fibers in the FIG. 1 catheter;

FIGS. 5A and 5B are sectional views similar to FIG. 2, on a smaller scale, illustrating different catheter embodiments.

DESCRIPTION OF THE PREFFERED EMBODIMENTS

Figure 1:
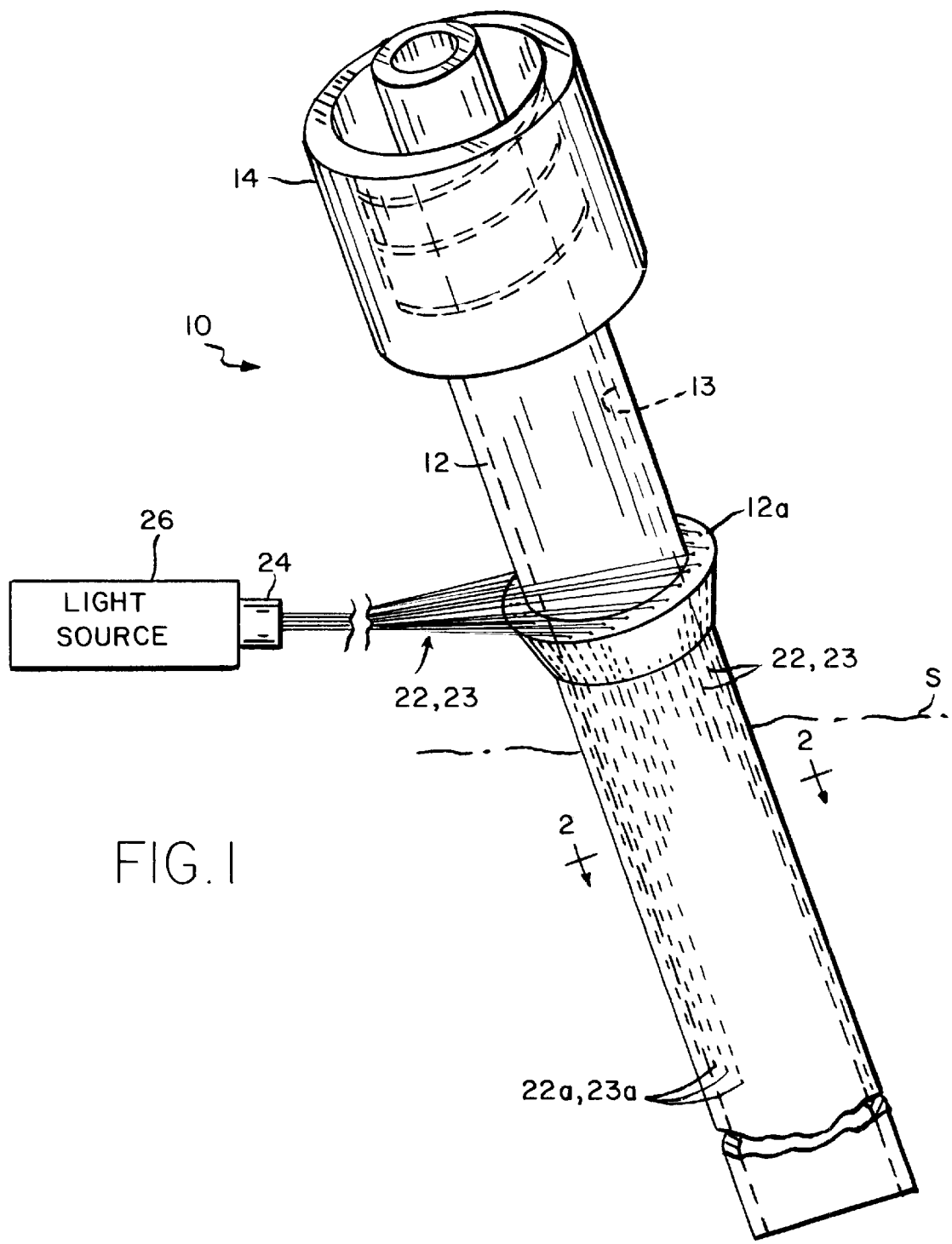
FIG. 1 is a perspective view with parts broken away showing a medical catheter incorporating the invention.

Referring now to FIG. 1 of the drawings, a catheter incorporating the invention, shown generally at 10, comprises a cannula 12. While the cannula is shown as having a single lumen 13, cannulas having a plurality of lumens are also within the scope of this invention. In any event, a standard medical connector or fitting 14 may be provided at the proximal end of cannula 12.

When extruding cannula 12, a multiplicity of tiny optical fibers 22, 23 are incorporated into the cannula wall. As shown in FIG. 2, fibers 22 and 23 are arranged in radially outer and inner circular arrays within that wall. Preferably also, the two circular arrays of fibers are staggered as shown in that figure. In some applications, the cannula 12 may contain three or more of such circular arrays of fibers.

Preferably fibers 22, 23 have various lengths. In other words the distal ends 22a of fibers 22 are located at various positions along the length of cannula 12; so too the ends 23a of fibers 23. FIG. 4 shows graphically typical positions for the distal ends 22a, 23a of the fibers. As seen there, those ends are distributed along the length of, and around the circumference of, the cannula. The ends may cover the entire in-dwelling segment of the catheter which is the segment below the skin line S shown in FIG. 1. Alternatively, they may cover only the segment of the catheter adjacent the skin line S.

As seen in FIG. 1, the optical fibers 22, 23 exit cannula 12 at a shoulder 12a. The proximal ends of the fibers 22, 23 are collected at a connector 24 which is optically matched to a light source 26 as is customary in the art. Light source 26 may comprise any suitable device that emits light energy in the desired spectral range including a laser, light emitting diode, or a fluorescent, halogen or incandescent bulb. The wavelength of the emitted light may be narrow spectrum, broad spectrum or a combination of same. Moreover, the light source 26 should be able to deliver the light energy either constantly or intermittently as pulses.

Instead of having the light source 26 separate from cannula 12 and connected thereto by optical fiber extensions or light pipes as shown in FIG. 1, the source 26 may consist of one or more light emitting diodes mounted directly to cannula 12 and optically coupled at cannula shoulder 12a to the input ends of fibers 22, 23 as indicated in phantom at 26 in FIG. 1.

When light source 26 is energized, light is coupled by fibers 22, 23 along the in-dwelling segment of cannula 12 to the distal ends 22a, 23a of the respective fibers. While those ends may be squared off, more preferably they are cut on a bias as shown in FIG. 3 so that there is a lateral component of the emitted light. Those end facets may be oriented to face radially outward so that the light emitted therefrom illuminates the outer surface of cannula 12. Alternatively, those facets may face inward so as to illuminate the wall of lumen 13. As a third possibility, the lower ends of fibers 22 may face outward and those of fibers 23 may face inward so that both surfaces of cannula 12 receive light energy from light source 26.

If desired, one or more conventional light or power taps may be formed along the lengths of the optical fibers 22, 23, as shown in doffed lines at 22b, 23b in FIG. 3 to provide additional light energy sources along the wall of cannula 12. To tap clad optical fiber light pipes or waveguides all or most of the outer cladding is removed from the fiber in the vicinity of the tap to accommodate a refractor which extracts power directly from the inner core of the fiber; see U.S. Pat. No. 4,842,356. Alternatively, the fiber may be bent in the vicinity of the tap to cause a portion of the light energy to radiate out from the inner core so that it can be extracted by the refractor; see e.g. U.S. Pat. No. 3,931,518.

The optical fibers 22, 23 may be of any material that can carry light of the desired wavelength(s). Although substances such as nylon or silica may be used, medical grade plastics (e.g. polytetrafluoroethylene) are preferred because of their relatively low cost. However, if source 26 emits ultraviolet light, the fibers should be of glass or quartz because plastics are poor transmitters of ultraviolet light.

Cannula 12 is preferably of a base material which has low absorption at the wavelength of the light energy from source 26 and should scatter to some extent the light emitted at the distal ends 22a, 23a of the fibers 22, 23 in order to help improve the uniformity of the light output delivered to the cannula surface(s). Medical grade polyurethane or silicone would be suitable for this purpose.

Also, to improve the diffusion through the wall of cannula 12 of the light emitted at the fiber ends 22a, 23a, radiation scattering material appropriate to the wavelength of the light energy from source 26 may be incorporated into the wall of cannula 12 as shown at 28 in FIG. 2. For example, the material may be light scattering particles of the type use in photodynamic therapy. Alternatively, the scattering material 28 may consist of a multiplicity of tiny light scattering fibers of the type available, for example, from Walsh Medical Devices, Inc., Ontario, Canada. In any event, the material 28 helps to diffuse light energy to the surface(s) of the cannula so that when light source 26 is energized, maximum light energy is conducted to one or both surfaces of cannula 12.

As alluded to above, light energy has to illuminate only those portions of the cannula surface(s) where such microorganisms are likely to grow. For example, it may only be necessary to illuminate the cannula wall surface(s) at the site where the catheter enters the body, e.g. adjacent to the skin line S in FIG. 1. In other cases, it may be desirable to illuminate the surface(s) along substantially the entire length of cannula 12 below its shoulder 12a.

Actually, the invention may be applied to a cuff for an indwelling device and fitted with optical fibers so as to illuminate the exterior surface of the cuff so as to prevent colonization by microorganisms at the surface of the cuff.

Instead of incorporating the optical fibers directly into cannula 12 at the time of its manufacture, optical fibers may be applied to one or both surfaces of the cannula after it is formed. For example, FIG. 5A shows a cannula 12' having a multiplicity of tiny optical fibers 32 adhered to the outside of the cannula and covered by a protective plastic sheath 34. A similar arrangement may be used to prevent the colonization by microorganisms of the outer surface of a medical device such as a stent or pacing lead or to provide a cuff on a percutaneous member where it passes through the skin line S in FIG. 1. FIG. 5B shows a cannula 12" whose inner surface is covered with optical fibers 36. Fibers 32 and 36 may be similar to fibers 22, 23 and operate in the same way to emit light energy that kills microorganisms tending to form at the adjacent surfaces of cannulae 12' and 12".

Further in accordance with the invention, the external and/or internal surface of the cannula may be provided with a coating 42 (FIG. 2) of a photosensitizer(s) activated by the light energy from source 26. Although a variety of photosensitizers may be used, the ideal photosensitizer(s) should be of low toxicity to mammalian cells, of broad antibacterial activity and activated at relatively low levels of light energy. One agent that meets these criteria is dimethyl-methylene blue. Other methylene blue derivatives alone or combined with another substance (e.g. toluidine blue O) could be used. In addition, dyes of the triarylmethane group (crystal violet and gentian violet) would also be effective. Other useful compounds are in the families of the cyanines, the phthalocyanines, and the perylenequinonoids. Cationic agents are, in general, more likely to enter a microorganism and to result in their death. A combination of two or more photosensitizers would broaden the antimicrobial activity of the catheter or device and make development of resistance less likely.

Preferably such photosensitizer(s) would be bound by an appropriate biologically inert material such as silastic or collagen and applied to one or both surfaces of cannula 12 to form the coating(s) 42.

It is also possible to incorporate the photosensitizer(s) directly into the wall of cannula 12. For example, a lipophilic cationic photosensitizer such as dimethyl-methylene blue may be incorporated into the plastic material of which cannula 12 is made at the time of the manufacture of the material.

In any event, the presence of light energy from source 26 at one or both surfaces of cannula 12 either directly kills the microorganisms on the surface(s) or activates the photosensitizer(s) on or in the cannula which would act (in most cases) by releasing activated oxygen to destroy the microorganisms present on the surface(s) and on the adjacent surface of fluid or tissue in or around the cannula.

It is believed that two possible activity modes are operative here. In the first mode, the photosensitizer is in or on the catheter, e.g. of polyurethane, the toxic singlet oxygen is generated by the effect of the light and then oxygen diffuses to the surface and interacts with the bacteria. It is believed that a phenothiazinium photosensitizer such as toluidine blue O with 620–630 nm light operates in this fashion. In the second mode, the photosensitizer is in the catheter or coating, diffuses to the surface and is taken up by the bacteria. Under the influence of the light, the toxic oxygen radical is then produced right in the bacterium. It is believed that the photosensitizer Rose Bengal in conjunction with 540–550 nm light operates in this way.

In either event, the catheter destroys the microorganisms on and around the cannula 12 at the implantation site and thus helps to prevent infection there.

Figure 6:
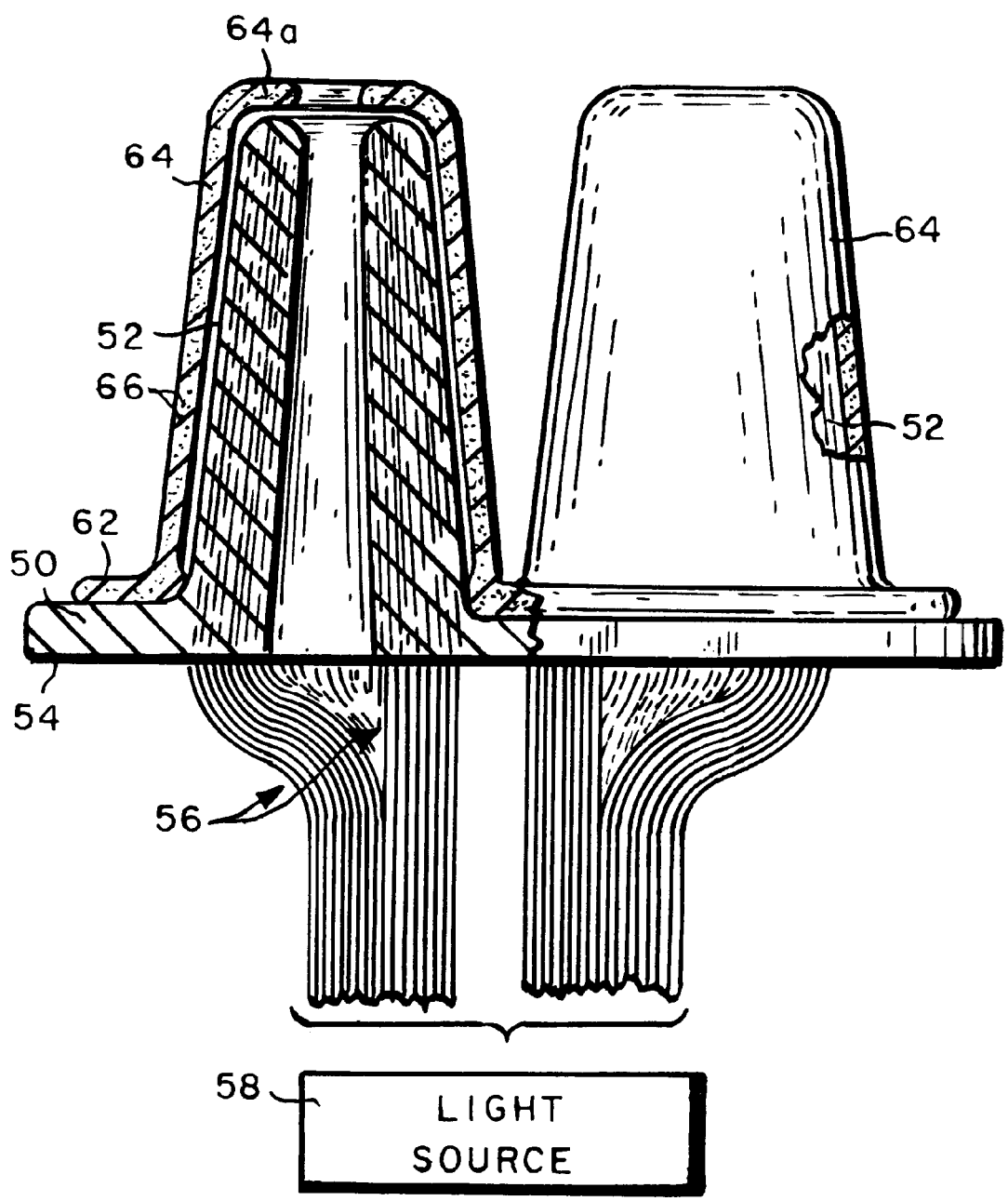
FIG. 6 is a sectional view of a nasal applicator incorporating the invention.

Refer now to FIG. 6 which depicts a medical device in the form of a nasal applicator for simultaneously delivering a photosensitizer and complementary light energy to the nasal epithelium to destroy bacteria such as *Staphylococcus aureus* in the anterior nares. The applicator comprises a molded plastic core 50 including a pair of side-by-side cannulae 52, 52 extending up from a base 54. Preferably, the cannulae are spaced apart, dimensioned and tapered to fit in the anterior nares.

Each cannula 52 contains in its walls optical fibers 56 similar to fibers 22, 23 or 32 described above. These fibers receive light from a suitable light source 58 and have light taps so that light is transmitted to the outer surfaces of the cannulae. Alternatively, tiny LEDs may be incorporated into the cannula walls and connected to a suitable energy source to provide such light.

The applicator preferably also includes a disposable photosensitive cover member 62 which fits snugly over the core 50. Cover member 62 consists of a thin, molded plastic shell formed with two parallel sheaths 64 which fit on the cannulae 52. The sheaths 64 have openings 64a opposite the upper ends of the cannulae that are aligned with the cannulae passages to allow breathing through the nose. Cover member 62, or at least the sheaths 64 thereof, contains at least one photosensitizer agent 66, e.g. methylene blue, in a suitable concentration. Alternatively, the shell may have a photosensitive coating 42 as described above in connection with FIG. 2. When the applicator is placed in the nose and source 58 is operating, fibers 56 direct light to the cover member 62 whose wavelength is such as to release the photosensitive agent 66 to the surface of the nasal tissue adjacent to the applicator thereby destroying any nasal staphylococcus therein.

It will thus be seen that the objects set forth above, among those made apparent from the preceding description are efficiently attained. Also, certain changes may be made in the carrying out the above method and in the constructions set forth without departing from the scope of the invention. For example, instead of employing many light fibers to conduct light along the catheter wall, a single light pipe spiraling along the catheter may be provided with a multiplicity of light taps to provide the necessary light to activate the photosensitizer. Also, the medical device instead of being tubular, may be a solid instrument such as a probe. Therefore, it is intended that all matter contained in the above description or shown in the accompanying drawings shall be interpreted as illustrative and not in a limiting sense.

It is also to be understood that the following claims are intended to cover all of the generic and specific features of the invention described herein.

What is claimed is:

1. Medical apparatus for placement in the human body comprising
   a member having an exterior surface adapted for physiological contact;
   at least one photosensitizer at or in said exterior surface;
   at least one light conductor extending along said member, each light conductor having an input at a proximal location along said member and an output at a distal location along said member, and
   a light transmitter for transmitting light energy to said input of the light conductor so that said light energy is conveyed along said member and is emitted at said output so as to illuminate said surface and said photosensitizer(s) residing on or in said exterior surface, the light energy being in a wavelength range to both activate the photosensitizer(s) so as to release toxic oxygen from said surface and also kill microorganisms on or opposite said surface.

2. The apparatus defined in claim 1 wherein said wavelength range is 200 nm to 1400 nm.

3. The apparatus defined in claim 1 wherein said at least one photosensitizer is selected from the group consisting of dimethyl-methylene blue, toluidine blue O, crystal violet, gentian violet, phenothiazinium, phthalocyanines and perylenequinonoids.

4. The apparatus defined in claim 1 wherein the photosensitizer is coated on said surface.

5. The apparatus defined in claim 1 wherein the photosensitizer is imbedded in said member.

6. The apparatus defined in claim 1 wherein the photosensitizer is incorporated in a removable sheath covering said member at said surface.

7. The apparatus defined in claim 1 wherein the apparatus is a nasal applicator and the member comprises a cannula insertable into a nasal passage.

8. The apparatus defined in claim 1 wherein the member comprises a probe.

9. The apparatus defined in claim 1 wherein the member is tubular and at least one light conductor is a spiral light pipe extending along said member and having a plurality of light taps along its length which direct light to said surface.

10. Medical apparatus for placement in the human body comprising
    a wall with interior and exterior surfaces;
    light energy conductors extending along at least an implantable segment of said wall, said conductors having inputs at a proximal location along said wall and outputs at a distal location along said wall;
    at least one photosensitizer on or in said wall segment, said at least one photosensitizer, when illuminated by complementary light energy, releasing activated oxygen radicals which destroy microorganisms, and
    a light source for delivering complementary light energy to said inputs so that said complementary light energy is conveyed along said wall segment and is emitted at said outputs thereby illuminating the at least one photosensitizer residing on or in said wall segment and at least one of said surfaces, the complementary light energy being in a wavelength range to both activate the photosensitizer so as to release said oxygen radicals and also kill microorganisms on and opposite said at least one of said surfaces.

11. The apparatus defined in claim 10 wherein said wavelength range is 200 nm to 1400 nm.

12. The apparatus defined in claim 10 wherein said at least one photosensitizer is coated on at least one surface of the wall.

13. The apparatus defined in claim 10 wherein said at least one photosensitizer is coated on both surfaces of the wall.

14. The apparatus defined in claim 10 wherein said at least one photosensitizer is located in said wall.

15. The apparatus defined in claim 10 wherein said at least one photosensitizer is selected from the group consisting of dimethyl-methylene blue, toluidine blue O, crystal violet, gentian violet, phenothiazinium, phthalocyanines and perylenequinonoids.

16. The apparatus defined in claim 10 wherein said wall defines a catheter.

17. The apparatus defined in claim 10 wherein said wall defines a cannula insertable into a nasal passage.

18. The apparatus defined in claim 10 wherein said conductors comprise a plurality of optical fibers extending along said wall, said fibers having output ends directed to at least one of said surfaces.

19. The apparatus defined in claim 18 wherein said fibers extend along the wall between said surfaces thereof.

20. The apparatus defined in claim 18 wherein said fibers extend along the wall at a surface thereof.

21. The apparatus defined in claim 18 wherein said fibers extend along the wall at both surfaces thereof.

22. The apparatus defined in claim 18 wherein said fibers have output ends which are cut on a bias and face said at least one of said surfaces.

23. The apparatus defined in claim 18 wherein said fibers have output ends which are square cut.

24. The apparatus defined in claim 18 wherein the plurality of optical fibers have various lengths.

25. The apparatus defined in claim 18 wherein said optical fibers have one or more light taps along their lengths which face said at least one of said surfaces.

26. The apparatus defined in claim 18 wherein the output ends of said fibers are distributed over substantially the entire surface area of the wall.

27. The apparatus defined in claim 10 wherein said light source is selected from the group consisting of laser, incandescent, fluorescent or halogen bulb and light emitting diode.

28. The apparatus defined in claim 27 wherein the light source is mounted to said wall and connected directly to the inputs of said conductors.

29. The apparatus defined in claim 27 wherein the light includes an illuminator and light pipes extending from said illuminator to the input of said conductors.

30. The apparatus defined in claim 27 wherein said light source is a pulsed source which delivers said light energy as pulses.

31. The apparatus defined in claim 27 wherein said light source is a constant light source which transmits constant light energy.

32. The apparatus defined in claim 10 and further including light scatterers incorporated into said wall for scattering light emitted at the outputs of said conductors.

33. The apparatus defined in claim 32 wherein said light scatterers comprise a multiplicity of tiny fibers selected from the group consisting of plastic, quartz and glass fibers.

34. A method of preventing infections comprising the steps of forming a member with at least one light energy conductor extending along at least a segment of the member, each conductor having an input at a proximal location along the member and an output at a distal location along the member;

incorporating at least one photosensitizer on or in said segment;

placing the segment in the body, and transmitting light energy to each input so that the light energy is conveyed along the segment and is emitted at the output so as to illuminate a surface of the member, the light energy being in a wavelength range to both activate the photosensitizer residing on or in said segment so as to release toxic oxygen and also kill microorganisms on and opposite the surface.

35. The method defined in claim 34 including the step of selecting the photosensitizers from the group consisting of dimethyl-methylene blue, toluidine blue O, crystal violet, gentian violet, phenothiazinium, phthalocyanines and perylenequinonoids.

36. The method defined in claim 35 including the step of selecting said range between 200 nm and 1400 nm.

* * * * *